(12) United States Patent
Fan et al.

(10) Patent No.: US 10,657,786 B2
(45) Date of Patent: May 19, 2020

(54) INFANT HEALTH MONITOR PATCH WITH MICROPHONE

(71) Applicants: Victoria H. Fan, Stanford, CA (US); Russell D. Fernald, Stanford, CA (US)

(72) Inventors: Victoria H. Fan, Stanford, CA (US); Russell D. Fernald, Stanford, CA (US)

( * ) Notice: Subject to any disclaimer, the term of this patent is extended or adjusted under 35 U.S.C. 154(b) by 702 days.

(21) Appl. No.: 15/365,957

(22) Filed: Dec. 1, 2016

(65) Prior Publication Data
US 2018/0158303 A1 Jun. 7, 2018

(51) Int. Cl.
| | | |
|---|---|---|
| *G08B 21/02* | (2006.01) | |
| *A61N 1/36* | (2006.01) | |
| *A61B 5/00* | (2006.01) | |
| *A61B 5/024* | (2006.01) | |
| *A61H 39/00* | (2006.01) | |
| *A61B 7/04* | (2006.01) | |

(Continued)

(52) U.S. Cl.
CPC ........ *G08B 21/0211* (2013.01); *A61B 5/0015* (2013.01); *A61B 5/02438* (2013.01); *A61B 5/6833* (2013.01); *A61B 5/6838* (2013.01); *A61B 5/746* (2013.01); *A61B 7/04* (2013.01); *A61H 39/00* (2013.01); *G08B 21/023* (2013.01); *G08B 21/0208* (2013.01); *G08B 21/0252* (2013.01); *G08B 21/0291* (2013.01); *A61B 5/741* (2013.01); *A61B 5/742* (2013.01); *A61B 2503/04* (2013.01); *A61H 2201/0169* (2013.01); *A61H 2201/0184* (2013.01); *A61H 2201/1207* (2013.01); *A61H 2201/165* (2013.01); *A61H 2201/1697* (2013.01); *A61H 2201/50* (2013.01); *A61N 1/3625* (2013.01); *A61N 1/3904* (2017.08)

(58) Field of Classification Search
CPC .................................................. A61N 1/36014
See application file for complete search history.

(56) References Cited

U.S. PATENT DOCUMENTS

| | | | | |
|---|---|---|---|---|
| 5,684,460 | A * | 11/1997 | Scanlon | A61B 5/113 340/573.1 |
| 7,733,233 | B2 * | 6/2010 | O'Shea | A61B 5/0002 340/573.7 |

(Continued)

*Primary Examiner* — Matthew F Desanto
(74) *Attorney, Agent, or Firm* — Keith Miller Patent Law, PLLC; Keith Miller

(57) ABSTRACT

The system of the preferred embodiments is a young child monitoring device including: at least one microphone designed to be temporarily attached in contact with at least one of the skin and the clothing of a user; a radio transmission circuit wired in electrical communication with the microphone and adapted to transmit a signal from the microphone via radio waves; an electromagnetic induction circuit designed to generate power by induction from radio waves; a temporary attachment including at least one of A) an adhesive patch, B) a clip, C) adhesive tape, D) a patch comprising at least the hooks of a hook and loop fastener and designed to attach at least the microphone to the user; a base station including a radio receiver adapted to receive a signal generated by the radio transmission circuit, wherein the base station is designed to at least one of I) notify a caregiver, II) generate an audio alert, III) generate a visual alert, IV) send an alert to a mobile electronic device associated with a caregiver, V) send an alert to a headset worn by a caregiver and adapted to play audio for the caregiver.

19 Claims, 1 Drawing Sheet

(51) Int. Cl.
*A61N 1/39* (2006.01)
*A61N 1/362* (2006.01)

(56) References Cited

U.S. PATENT DOCUMENTS

| | | | |
|---|---|---|---|
| 2006/0197671 A1* | 9/2006 | Groover | G08B 21/0208 340/573.1 |
| 2009/0040044 A1* | 2/2009 | Chiao | A61B 5/0002 340/540 |
| 2009/0207014 A1* | 8/2009 | Ayed | G08B 13/1427 340/539.13 |
| 2010/0217158 A1* | 8/2010 | Wolfe | A61B 5/113 600/595 |
| 2012/0232398 A1* | 9/2012 | Roham | A61B 8/0866 600/453 |
| 2016/0324466 A1* | 11/2016 | Chang | A61B 5/4818 |

* cited by examiner

INFANT HEALTH MONITOR PATCH WITH MICROPHONE

DESCRIPTION OF THE PREFERRED EMBODIMENTS

The description that follows of the invention's preferred embodiments is meant to enable someone skilled in the prior art to make and use the invention, but is not meant to limit the invention to these preferred embodiments.

1. First Preferred Embodiment

Figure 1:
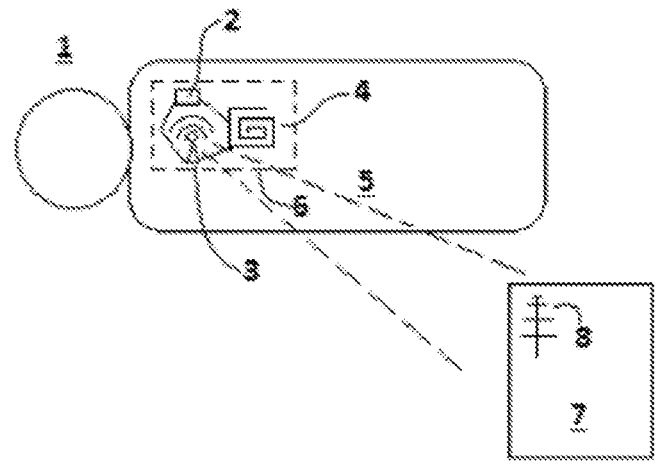
FIG. 1 is a schematic representation of the system of the first preferred embodiments.

As shown in FIG. 1, the system of the preferred embodiments is a young child monitoring device 1 including: at least one microphone 2 designed to be temporarily attached in contact with at least one of the skin and the clothing of a user 5; a radio transmission circuit 3 wired in electrical communication with the microphone 2 and adapted to transmit a signal 11 from the microphone 2 via radio waves; an electromagnetic induction circuit 4 designed to generate power by induction from radio waves; a temporary attachment 6 including at least one of A) an adhesive patch, B) a clip, C) adhesive tape, D) a patch comprising at least the hooks of a hook and loop fastener and designed to attach at least the microphone 2 to the user 5; a base station 7 including a radio receiver 8 adapted to receive a signal 11 generated by the radio transmission circuit 3, wherein the base station 7 is designed to at least one of I) notify a caregiver 19, II) generate an audio alert, III) generate a visual alert, IV) send an alert to a mobile electronic device 18 associated with a caregiver 19, V) send an alert to a headset 13 worn by a caregiver 19 and adapted to play audio for the caregiver 19. The system of the preferred embodiments is preferably designed to monitor a young child to prevent and possibly intervene to stop sudden infant death syndrome. The system of the preferred embodiments may, however, be used for any suitable purpose.

Figure 2:
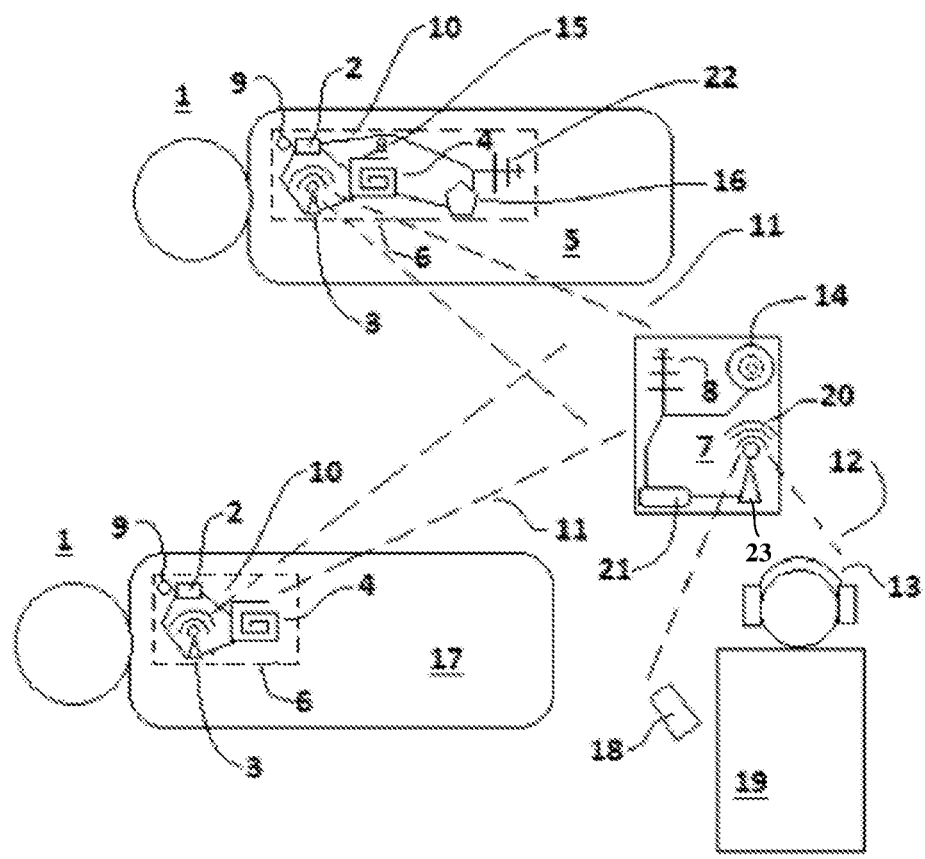
FIG. 2 is a schematic representation of the system of the first preferred embodiments, where at least two users are covered by at least one base station, the caregiver has at least one of a headset and a mobile electronic device in communication with the base station, and there are additional variation features such as a stimulus device.

As shown in FIG. 1, the system of the preferred embodiments uses a microphone 2 held against at least one of the user's 5 skin and the user's 5 clothing to monitor vital signs of a user 5. In a preferred embodiment, the vital signs include a user's 5 heartbeat. The vital signs may, however, include any suitable functions of the user's 5 body. Preferably a signal 11 from the microphone 2 is transmitted to the radio receiver 8 in the base station 7 by the radio transmission circuit 3 wired in electrical communication to the microphone. In a preferred variation as shown in FIG. 2, the base station 7 also includes a radio transmitter 20 wired in electrical communication to the radio receiver 8 in the base station 7, and at least one of the signal 11 from the microphone 2 and data related to the signal 11 from the microphone 2 is transmitted by a radio transmitter 20 in the base station 7 to at least one of a mobile electronic device 18 associated with a caregiver 19, and a headset 13 associated with a caregiver 19. In a variation of this variation, this allows a caregiver 19 to listen to the heartbeat of a user 5 in real time. In one preferred variation the caregiver 19 listens directly to the heartbeat in order to provide information related to the well-being of the user 5, and assurance that the user 5 is healthy. In a variation of this variation, this information is used to monitor a young child user 5 for symptoms that may be related to sudden infant death syndrome, known as SIDS. The base station 7 may, however, use the signal 11 generated by the microphone 2 and transmitted to the base station 7 by the radio transmission circuit 3 in any suitable manner. There may, however, be any suitable form of playing audio for the caregiver 19, or none at all.

As shown in FIG. 2, in a preferred variation the base station 7 may include a speaker 14. In one preferred variation, the speaker 14 may be designed to provide an audio alert to at least one of the user 5 and the caregiver 19. In one preferred variation, the base station 7 may further include at least one of an analog signal processing circuit and a digital signal processing circuit 21 designed to detect an event that may be dangerous to the user 5 in the signal 11 coming from the microphone 2 and transmitted by the radio transmission circuit 3. In a variation of this variation, upon the detection of an event that is potentially dangerous to the user 5, the base station 7 may be designed to play an audio alert through the speaker 14. In a further variation of this variation, the audio alert may include a voice recording, which in a preferred variation may be a custom voice recording. In a further variation, the custom voice recording may be a recording of at least one of the user's 5 parents, as it is scientifically proven that particularly the voice of a child's mother speaking the child's name has a stronger effect in triggering neural activity in a child and bringing the child to alertness, which may help top a sudden infant death syndrome alert. In another preferred variation, as seen in FIG. 2, there may also be a stimulus device 16 attached at least to the temporary attachment 6 and held against the user's 5 body, where the stimulus device 16 is wired in electrical communication to a second radio receiver 22, wherein the base station 7 may send a signal to the second radio receiver 22 to trigger the activation of the stimulus device 16, where the stimulus device 16 is designed to create at least one of a physiological interruption and a neurological interruption to a sudden infant death syndrome event. In a preferred variation, the stimulus device 16 is designed to provide at least one of physical stimulus to the user 5 and electrical stimulus to the user 5. In a further preferred variation, the stimulus device 16 includes at least one of an electrical stimulation device designed to apply an electrical current that passes through at least a portion of the user's body, an AED device, a remote acupuncture device, and an actuator adapted to physically move the position of the user 5. There may, however, be any suitable stimulus device 16, including devices that have not yet been developed for correcting the physiology of a user 5 in a sudden infant death syndrome event, or no stimulus device 16 at all. The base station 7 may, however, process the signal 11 from the microphone 2 in any suitable way, or may not process the signal at all. In another variation, the system of the preferred embodiments may further include at least one of an analog signal processing circuit and a digital signal processing circuit 21 wired directly in electrical communication to the microphone, and attached to the temporary attachment 6, wherein the at least one of an analog signal processing circuit and a digital signal processing circuit 21 is designed to analyze the signal 11 from the microphone 2 to detect an event that may be dangerous to the user 5. There may, however, be no signal processing circuit whatsoever. The base station 7 may, however, provide any suitable alert to the caregiver 19, and transmit any suitable signal 12 or information to the caregiver 19. In another preferred variation the base station 7 may be further adapted to transmit data to an internet connection, allowing at least one of processing from cloud computing resources and access to data coming from the device via the internet.

As shown in FIG. 1, the temporary attachment 6 is designed to hold the electronic circuitry at least one of on the user 5 and near the user 5, and to hold the microphone 2 against at least one of the user's 5 skin and the user's 5 clothes. In a preferred variation, the temporary attachment 6 is an adhesive patch. In a further variation, the adhesive patch comprises a water-resistant adhesive but is also water permeable to provide breathability. In a preferred variation, the patch, microphone, and electronic circuitry comprising at least the radio transmission circuit 3 and the electromagnetic induction circuit 4 are designed to be of sufficiently low cost to be disposable. In another preferred variation, the temporary attachment 6 may include the loop side of a hook and loop fastener to allow attachment to a user's 5 clothes. In another preferred variation, the temporary attachment 6 may be at least one of an elastic piece of clothing and an elastic fabric band. The temporary attachment 6 may, however, have any suitable design for holding the microphone 2 against at least one of the user's 5 skin and the user's 5 clothes.

As shown in FIG. 2, there is preferably a radio signal transmitter 23 in the base station 7, and the radio signal transmitted by the radio signal transmitter 23 in the base station 7 preferably has sufficient power and frequency to allow the electromagnetic induction circuit 4 to generate enough electrical power to power at least the microphone 2 and the radio transmission circuit 3. In a preferred variation the electromagnetic induction circuit 4 can power the electronic circuitry attached 10 to the user 5 from at least five feet away from the base station 7 by generating power from the signal transmitted by the radio signal transmitter 23 in the base station 7. In a further preferred variation, the electromagnetic induction circuit 4 can power the electronic circuitry attached 10 to the user 5 from at least twenty feet away from the base station 7. In a preferred variation, the radio signal transmitter 23 in the base station 7 is an enhanced near field communication transmitter. In one preferred variation, the radio signal transmitter 23 that provides the radio signal that the electromagnetic induction circuit 4 generates power from is separate from the radio signal transmitter 20 that transmits a signal 12 to at least one of a headset 13 associated with a caregiver 19 and a mobile electronic device 18 associated with a caregiver 19. In another preferred variation, there is only one radio signal transmitter 23 in the base station 7, and it is designed to transmit all signals 12 that the base station 7 must transmit. There may, however, be any suitable arrangement of radio signal transmitters on the base station 7.

As shown in FIG. 2, in one preferred variation, the base station 7 may be able to receive signals 11 from at least two microphones 2 attached to at least two users. In this preferred variation, a caregiver 19 may be enabled to monitor a user 5 and at least one additional user 17 through one base station 7, and one base station 7 may be able to detect and alert for dangerous events concerning at least two users.

As shown in FIG. 2, in one preferred variation, at least one LED light 15 may be wired in electrical communication to the electromagnetic induction circuit 4 to alert a caregiver 19 to the proper functioning of the electronic circuitry attached 10 to the user 5. In a variation of this variation, a red and green LED light 15 may be attached to the electromagnetic induction circuit 4 to provide a red light if the device is not functioning properly, and a green light if it is.

As shown in FIG. 2, in one preferred variation there may also be at least one of noise canceling and noise filtering circuitry 9 wired in electrical communication to the microphone 2 to reduce the noise in the signal produced by the microphone 2. In a further variation of this variation, there may be at least two microphones 2 wired in electrical communication to the at least one of noise canceling and noise filtering circuitry 9, allowing better noise removal from the signal.

In a preferred variation, an automatic electronic defibrillator (AED) may also be attached to the temporary attachment 6 and designed to provide immediate resuscitation in an emergency situation. In a variation of this variation, the base station 7 may detect conditions indicating an emergency situation from the transmitted signal 11 and then transmit a signal to the AED in order to activate the AED to create a physiological interruption to the emergency situation in an attempt to aide the user.

In a further preferred variation, there may be a camera wired in electrical communication with at least the electromagnetic induction circuit 4 and the radio transmission circuit 3.

In a further preferred variation, there may be signal processing and amplification circuitry included in the base station 7 and wired in electrical communication to the radio receiver 8 in the base station 7 to improve the signal received from the at least one microphone.

As a person skilled in the art will recognize from the previous detailed description and from the figures and claims, modifications and changes can be made to the preferred embodiments of the invention without departing from the scope of this invention defined in the following claims.

We claim:

1. A child monitoring device comprising:
a microphone configured to be temporarily connected to a user;
electronic circuitry including a radio transmission circuit coupled in electrical communication with the microphone and configured to transmit a first signal from the microphone via radio waves, and an electromagnetic induction circuit configured to generate power by induction from the radio waves;
a temporary attachment comprising an adhesive patch, wherein the microphone and the electronic circuitry are secured to is embedded in the temporary attachment and the temporary attachment is disposable;
a first electrical stimulus device attached in electrical communication to at least the electromagnetic induction circuit, wherein the first electrical stimulus device is configured to be held against the skin of the user by the temporary attachment and apply an electronic current into the skin or provide resuscitation; and
a base station comprising a radio receiver and a radio transmitter, the radio receiver is configured to receive the first signal generated by the radio transmission circuit, wherein the base station is configured to perform at least one of notifying a caregiver, generating an audio alert, generating a visual alert, sending a mobile device alert to a mobile electronic device associated with the caregiver, and sending a headset alert to a headset worn by the caregiver and configured to play audio for the caregiver and the radio transmitter is configured to transmit a radio signal of a frequency that will cause a first amount of induction in the electromagnetic induction circuit that is sufficient to generate first amount of power that is sufficient to run the electronic circuitry in the temporary attachment.

2. The child monitoring device of claim 1, wherein the base station is further configured to transmit an enhanced near field communication signal, and
wherein the electromagnetic induction circuit is further configured to generate a second amount of power from the enhanced near field communication signal transmitted by the base station that is sufficient to power the electronic circuitry in the temporary attachment when the electronic circuitry is at a distance of at least 5 feet from the base station.

3. The monitoring device of claim 2, wherein the microphone comprises at least one of noise canceling circuitry and noise filtering circuitry configured to improve the signal from the microphone,
wherein the base station further comprises a radio signal transmitter configured to transmit an audio signal from the microphone to the headset worn by the caregiver, and
wherein the headset is configured to allow the caregiver to listen to the audio signal and to monitor a heartbeat of the user.

4. The monitoring device of claim 3, wherein the base station further comprises at least one of an analog signal processing circuit and a digital signal processing circuit attached in electrical communication to the radio receiver configured to detect, from the first signed coming from the microphone, an event that is dangerous to the user; and
wherein the base station further comprises a speaker that is configured to play the audio alert when the event that is dangerous to the user is detected.

5. The child monitoring device of claim 4, wherein the audio alert includes a custom voice recording.

6. The monitoring device of claim 5, wherein the custom voice recording is a recording from at least one parent of the user.

7. The child monitoring device of claim 6, wherein the electronic circuitry further comprises at least one LED configured to indicate to the caregiver that the child monitoring device is functioning properly.

8. The child monitoring device of claim 3, further comprising:
a second stimulus device;
at least one of a first analog signal processing circuit and a first digital signal processing circuit attached in electrical communication to the microphone and the first electrical stimulus device, wherein the at least one of the first analog signal processing circuit and the first digital signal processing circuit is configured to:
detect, from the first signal coming from the microphone attached to the user, an event that is dangerous to the user, and
send an activation signal to a second radio receiver attached in electrical communication to the first electrical stimulus device.

9. The child monitoring device of claim 8, wherein the first electrical stimulus device is an electrical stimulation device or an automatic electronic defibrillator device and the second stimulus device comprises at least one of a remote acupuncture device configured to physically move the respective user, and an actuator configured to physically move a position of the respective user.

10. The child monitoring device of claim 2, wherein the base station further comprises at least one of an analog signal processing circuit and a digital signal processing circuit attached in electrical communication to the radio receiver and configured to detect, from the first signal coming from the microphone, an event that is dangerous to the user; and
wherein the base station further comprises a speaker that is configured to play the audio alert when the event that is dangerous to the user is detected.

11. The child monitoring device of claim 10, wherein the audio alert includes a custom voice recording.

12. The child monitoring device of claim 11, wherein the custom voice recording is a recording from at least one of the user's parents.

13. The child monitoring device of claim 1, wherein the base station further comprises at least one of an analog signal processing circuit and a digital signal processing circuit attached in electrical communication to the radio receiver and configured to detect, from the first signal coming from the microphone, an event that is dangerous to the user; and
wherein the base station further comprises a speaker that is configured to play the audio alert when the event that is dangerous to the user is detected.

14. The child monitoring device of claim 13, wherein the audio alert includes a custom voice recording.

15. The child monitoring device of claim 14, wherein the custom voice recording is a recording from at least one parent of the user.

16. The child monitoring device of claim 1, wherein the microphone comprises at least one of noise canceling circuitry and noise filtering circuitry configured to improve the signal from the microphone.

17. The child monitoring device of claim 16, wherein the base station further comprises a radio signal transmitter configured to transmit an audio signal from the microphone to the headset worn by the caregiver;
wherein the headset is configured to allow the caregiver to listen to the audio signal and to monitor a heartbeat of the user.

18. The child monitoring device of claim 1, further comprising,
wherein at least one of an analog signal processing circuit and a digital signal processing circuit attached in electrical communication to the microphone and to the first electrical stimulus device, wherein the at least one of an analog signal processing circuit and a digital signal processing circuit is configured to:
detect, from the first signal coming from the microphone, an event that is dangerous to the user, and
send an activation signal to the first electrical stimulus device
wherein the first stimulus device is configured to provide a physical stimulus to the user that is at least one of a physical stimulus and an electrical stimulus, and wherein the first electrical stimulus device is configured to create at least one of a physiological interruption and a neurological interruption to a sudden infant death syndrome (SIDS) event.

19. The child monitoring device of claim 18, wherein the first electrical stimulus device is further configured to be in electrical communication with the base station and a second radio receiver, and
wherein the base station is further configured to receive a second signal generated by a second radio transmission circuit transmitting the second signal from a second microphone attached to a second user.

\* \* \* \* \*